United States Patent
Neilan et al.

(10) Patent No.: US 11,752,019 B2
(45) Date of Patent: Sep. 12, 2023

(54) BIOACTIVE AGENT COATED MEDICAL DEVICE AND METHOD OF COATING SUCH A DEVICE

(71) Applicant: Cook Medical Technologies LLC, Bloomington, IN (US)

(72) Inventors: John Neilan, Gort (IE); David Murray, Limerick (IE); James Butler, Aherlow (IE)

(73) Assignee: Cook Medical Technologies LLC, Bloomington, IN (US)

(*) Notice: Subject to any disclaimer, the term of this patent is extended or adjusted under 35 U.S.C. 154(b) by 50 days.

(21) Appl. No.: 16/203,892

(22) Filed: Nov. 29, 2018

(65) Prior Publication Data
US 2020/0170814 A1     Jun. 4, 2020

(30) Foreign Application Priority Data
Nov. 29, 2018 (GB) ...................................... 1819449

(51) Int. Cl.
| | |
|---|---|
| *A61F 2/90* | (2013.01) |
| *A61L 29/16* | (2006.01) |
| *C22C 19/03* | (2006.01) |
| *A61L 31/02* | (2006.01) |

(52) U.S. Cl.
CPC ................ *A61F 2/90* (2013.01); *A61L 29/16* (2013.01); *A61L 31/022* (2013.01); *C22C 19/03* (2013.01); *A61L 2300/606* (2013.01)

(58) Field of Classification Search
CPC .............. A61F 2/90; A61L 31/08; B05D 5/00
See application file for complete search history.

(56) References Cited

U.S. PATENT DOCUMENTS

| | | |
|---|---|---|
| 4,539,061 A | 9/1985 | Sagiv |
| 6,632,470 B2 | 10/2003 | Morra et al. |
| 7,396,582 B2 | 7/2008 | Claude et al. |

(Continued)

FOREIGN PATENT DOCUMENTS

| | | |
|---|---|---|
| EP | 0819446 A2 | 1/1998 |
| EP | 3192534 A1 | 7/2017 |

(Continued)

OTHER PUBLICATIONS

"Standard Specification for Chemical Passivation Treatments for Stainless Steel Parts", Designation A967-01, ASTM International.

*Primary Examiner* — Dah-Wei D. Yuan
*Assistant Examiner* — Andrew J Bowman
(74) *Attorney, Agent, or Firm* — Woodard, Emhardt, Henry, Reeves & Wagner, LLP

(57) ABSTRACT

A medical device such as a stent or medical balloon is functionalised prior to coating with a bioactive material, specifically by carboxylic acidification of the contact surface or surfaces of the medical device. The preferred process involves washing a stent or other medical device in a washing solution which may be sodium hydroxide, soaking in a carboxylic acid solution, rinsing in water to remove excess carboxylic acid, allowing to dry before applying a bioactive agent layer. It has been found that washing after functionalisation removes excess carboxylic acid and enhances the retention of bioactive agent on the contact surface or surfaces of the medical device leading to a more uniform and consistent layer of bioactive agent.

20 Claims, 8 Drawing Sheets

(56) References Cited

U.S. PATENT DOCUMENTS

| | | | |
|---|---|---|---|
| 7,597,924 B2 | 10/2009 | Kondyurin et al. | |
| 8,123,799 B1 | 2/2012 | Malik et al. | |
| 8,808,272 B2 | 8/2014 | Barry et al. | |
| 9,005,960 B2 | 4/2015 | Legeay et al. | |
| 9,795,721 B2 | 10/2017 | Kadowaki et al. | |
| 2003/0099712 A1* | 5/2003 | Jayaraman | A61K 45/06 |
| | | | 427/2.28 |
| 2004/0265571 A1* | 12/2004 | Schwartz | B05D 1/185 |
| | | | 428/333 |
| 2009/0171453 A1 | 7/2009 | Adams et al. | |
| 2015/0174298 A1 | 6/2015 | Brouzes et al. | |
| 2016/0355688 A1 | 12/2016 | Drumheller et al. | |
| 2017/0203011 A1* | 7/2017 | Neilan | A61L 29/16 |

FOREIGN PATENT DOCUMENTS

| | | |
|---|---|---|
| EP | 3363478 A1 | 8/2018 |
| EP | 3431113 A1 | 1/2019 |
| GB | 2564667 A | 1/2019 |
| GB | 1819449.8 | 5/2019 |

\* cited by examiner

BIOACTIVE AGENT COATED MEDICAL DEVICE AND METHOD OF COATING SUCH A DEVICE

CROSS REFERENCE TO RELATED APPLICATIONS

This application claims the benefit of Great Britain patent application No. 1819449.8 filed on Nov. 29, 2018 entitled "BIOACTIVE AGENT COATED MEDICAL DEVICE AND METHOD OF COATING SUCH A DEVICE" the entire contents of which are incorporated herein by reference.

TECHNICAL FIELD

The present invention relates to a coated medical device, particularly coated with a bioactive agent, and to a method of preparing and coating such a device. The invention can be used with implantable medical devices such as stents, stent grafts, vascular filters and plugs, valvuloplasty devices and so on. It can also be applied to medical devices intended to be deployed temporarily in a patient, such as angioplasty balloons, valvuloplasty balloons, medical device deployment balloons and the like.

BACKGROUND OF THE INVENTION

Coated medical devices, particularly endoluminally deployable medical devices, are known for a variety of medical applications. In the case of an implantable medical device, that is a device intended to be left in the patient permanently or over long periods of time, the device may be coated with one or more layers of drugs intended for long term drug administration to diseased tissue. Treatment of cancers is an example. In other examples, the coating is provided in order to treat adverse body reactions caused by the medical treatment or by long term presence of a foreign object in the body, such as initial reactive hyperplasia, inflammation, thrombosis, restenosis and so on. In these cases the medical device may be deployed long term or only temporarily in a patient.

It is important that a bioactive coating on a medical device is consistent and homogeneous over the associated surface or surfaces of the device, is reliably formed from one device to another, is sufficiently well held on the device during deployment, and can be administered into the patient at the desired rate once the device is deployed. For instance, a coating on an implantable device such as a stent, filter, vascular plug or the like may need to be released over an extended period of time such as weeks, months or years; whereas a coating on a medical balloon, such as an angioplasty balloon or a device delivery balloon, may need to be released over a period of seconds or minutes.

Applying a bioactive agent to an untreated surface of a medical device often fails to form a uniform or reliable coating, leading to variable bioactive or therapeutic results. This is particularly the case with lipophilic materials including, for instance, paclitaxel, which has been proven to be a very effective anti-restenosis drug.

Attempts have been made in the art to treat one or more surfaces of medical devices to improve their biocompatibility and also to seek to improve the adherence of one or more coatings onto the medical device. These known treatments, however, have failed to provide consistent, reliable and repeatable surface characteristics for many bioactive agents. Failure to provide an adequate coating can result in failure to meet the strict drug release required by the FDA USP pharmacopeia drug device requirements and that of other regulatory bodies.

Other attempts in the art have involved providing for containment of the bioactive agent, for instance in a containment device such as a polymer matrix, by applying an outer layer or coat over the layer of bioactive material, by encapsulating the bioactive agent in capsules or other carriers, and so on. Such containment mechanisms, which restrain the bioactive material on the device and control the release of the material into the patient, can often cause other clinical issues, including reduction in the amount of bioactive material that can be carried on the medical device and inadequate release rate of the bioactive material. Furthermore, the containment mechanism can act as a target for long term restenosis and other foreign body reactions. Despite such drawbacks, containment mechanisms are still often proposed in order to seek to overcome the difficulty of adequately holding the bioactive material to the medical device and of ensuring adequate dosage of bioactive material in order to try to meet regulatory criteria.

Some examples of known surface treatments are disclosed in: "Standard Specification for Chemical Passivation Treatments for Stainless Steel Parts", Designation A967-01, ASTM International; U.S. Pat. Nos. 8,808,272, 4,539,061, US-2016/0355688, U.S. Pat. No. 9,795,721, US-2015/0174298, EP-0,819,446, WO-2013/152713, U.S. Pat. Nos. 7,597,924, 7,396,582, 6,632,470, 8,123,799, 9,005,960 and US-2009/171453.

SUMMARY OF THE INVENTION

The present invention seeks to provide an improved coated medical device and method of preparing and coating such a device.

According to an aspect of the present invention, there is provided a method of coating a medical device having a structure for implantation or disposition inside a patient, the structure including at least one surface for coating, the method including the steps of: functionalising the at least one surface of the structure by subjecting the at least one surface to acidification by a carboxylic acid to form at least one acid functionalised surface; washing the at least one acid functionalised surface; and applying a bioactive agent layer directly on so as to overlie the at least one functionalised and cleaned surface.

Advantageously, the step of functionalising the at least one surface causes an increase in acidic polar components at the at least one surface.

While the invention focuses upon the treatment of at least one surface of the medical device, that is one or more surfaces that are intended to support a coating of bioactive material, it is to be understood that at least some of the steps of the method may be applied to the entirety of the medical device, irrespective of whether or not one or more treated surfaces is or are then coated with a bioactive agent layer.

Preferably, the method includes a further step of washing the medical device prior to the functionalisation step. This further washing step may comprise washing the at least one surface of the medical device in a solution of washing agent. The solution may be or include at least one of: sodium hydroxide, ethanol, Isopropanol (IPA), acetone, acetonitrile, hydrogen peroxide, sodium hypochlorite, a surfactant or boiling water. In one embodiment, the solution is a solution of sodium hydroxide at a ratio of 0.1 grams sodium hydroxide in 100 ml water. Advantageously, the at least one surface of the medical device solution may be bathed in solution for around 30 minutes prior to functionalisation.

The method advantageously includes the step of rinsing the at least one surface of the medical device subsequent to the pre-functionalisation washing step. The rinsing step may involve rinsing in water 10 times.

Preferably, the at least one surface of the medical device is subjected to functionalisation without drying following pre-functionalisation washing and optional rinsing.

The functionalisation preferably involves soaking the at least one surface of the medical device in a carboxylic acid. The soaking may be in a carboxylic acid solution for around 2 hours at 30° C., using preferably a 5% carboxylic acid solution.

The preferred embodiments functionalise the at least one surface by means of a citric acid solution.

In the preferred embodiments, the post-functionalisation washing step involves rinsing the at least one surface of the medical device in water.

It is preferred that the post-functionalisation washing step involves rinsing the at least one surface of the medical device around 10 times in water.

Preferably, the at least one surface is dried between the post-functionalisation washing step and the step of applying the bioactive agent layer.

The bioactive agent layer may:
a) consist of or be principally of bioactive material;
b) be or include a therapeutic substance;
c) be or include an anti-proliferative bioactive substance; or
d) be or include paclitaxel.

In the preferred embodiments, the bioactive agent layer is free of one or more of:
a) containment elements;
b) binding agents; and
c) time control release agents;
d) polymer or other matrix material.

The step of functionalising the at least one surface preferably does not remove or altering oxide on the at least one surface.

While citric acid is currently the preferred carboxylic acid for functionalisation, other acids have also been found to be effective, including: acetic acid, lactic acid, ascorbic acid, tannic acid, carboxylic acid, alginic acid, adipic acid, hyaluronic acid, acrylic acid, propionic acid and conjugates and derivatives thereof.

The medical device may be or include:
a) a stent or balloon;
b) a stent and wherein the structure is made of nickel titanium alloy;
c) a balloon and the coating includes an excipient.

The teachings herein also extend to a medical device having a structure as taught herein.

The inventors have discovered that a material improvement in surface energy and adhesion characteristics can be achieved by functionalising the surface or surfaces of the medical device with a carboxylic acid. In practice, such functionalization creates acid polar species on the surface(s), which bind by strong covalent or Lewis bonds to the conjugate bioactive material layer. The inventors have discovered that such functionalization can lead to increases in overall surface energies of around 50 Dynes/cm or more when measured by the OWRK method. This, coupled with the polar components created on the contact surface, forms a highly reactive surface to which the (bioactive) material layer binds. More particularly, the functionalisation taught herein amplifies the polar surface energy related to the type of functionalisation while suppressing other polar components of the surface energy. As described in detail below, acidification, for example, can increase the polar acid surface energy while reducing and in some cases completely suppressing the base polar components. As a result, it is not necessary to restrain the (bioactive) material in any containment mechanism, such as a containment polymer, matrix or the like.

It is preferred that the or each functionalised surface is substantially impervious to the material coating. In other words, it is preferred that the bioactive material is in the form of a distinct layer overlying the functionalised surface and preferably does not penetrate at all, or only minimally, into the functionalised surface.

Preferably, the entirety of the at least one surface is functionalised. This ensures a consistent and uniform coating of bioactive agent.

Advantageously, the coating is or includes a therapeutic substance. The coating may be or include an anti-proliferative bioactive substance, for instance paclitaxel or derivatives thereof. The coating may include one or more of a variety of other bioactive agents, of which examples are given below.

The method may also include the step of cleaning the at least one surface with an alcohol prior to functionalization, in order to remove contaminants from the surface. Advantageously, the step of cleaning the at least one surface with alcohol is carried out prior to any atomic cleaning of the surface. Ethanol is a suitable cleaning agent for this step.

The acids used for functionalisation of the surface may have a range of acidities. A strong acid, of around 1.5 pH acidity, is particularly effective. It is preferred that the at least one acidic component includes one or more of:

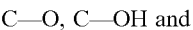 and

The at least one functionalised surface may also include a dispersal facilitator, such as a C—C component.

The medical device may be of any of the varieties described above and elsewhere in this specification. Examples include stents and medical balloons. Where the medical device is a stent or has a similar support member or scaffold, the medical device may be made of a metal or metal alloy, such as a nickel titanium alloy. The stent could equally be made of other materials known in the art.

Where the medical device is or includes a balloon, or otherwise would benefit from fast release of the bioactive material, the coating may include or overlie an excipient.

According to another aspect of the present invention, there is provided a medical device having a structure for implantation or disposition inside a patient, the structure including at least one coated surface, the at least one coated surface being carboxylic acid functionalised by a carboxylic acid layer 3o of up to 2.2 nanometres in thickness and being coated with a bioactive agent layer directly on the at least one functionalised surface.

Other aspects and advantages of the teachings herein are described below in connection with the preferred embodiments disclosed herein.

BRIEF DESCRIPTION OF THE DRAWING

Embodiments of the present invention are described below, by way of example only, with reference to the accompanying drawings, in which.

DETAILED DESCRIPTION

Figure 1:
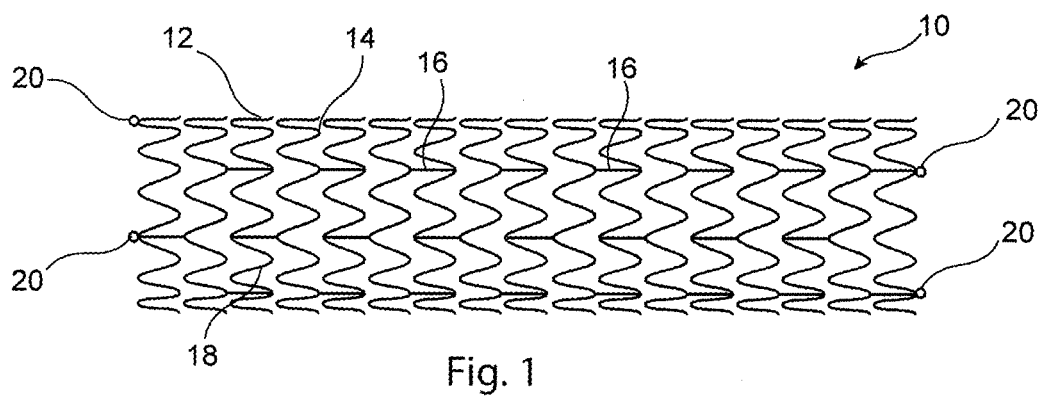
FIG. 1 is a side elevational view of an exemplary vascular stent.

It is to be understood that the drawings are schematic only and not to scale. Often only the principal components relevant to the teachings herein are shown in the drawings, for the sake of clarity.

The embodiments described below focus on a coated stent and a coated balloon. It is to be understood, however, that these are examples only and that the teachings herein can be applied to a large range of medical devices, both for temporary deployment in a patient and also for long term placement. Other examples include stent grafts, vascular filters and plugs, valvuloplasty devices, prostheses and so on.

The terms bioactive agent and bioactive material are used interchangeably in this specification and are intended to encompass materials, elements and compounds that have a therapeutic and/or preventative effect. They may, for example, be or include a therapeutic substance, such as an anti-proliferative bioactive substance of which paclitaxel is a preferred agent. Further examples of bioactive agents are given below and will also be apparent to the person skilled in the art.

Referring first to FIG. 1, there is shown an exemplary vascular stent 10 to which the teachings herein can be applied. The stent 10 is generally a tubular structure 12, in this example formed of a plurality of stent rings 14 that extend in series coaxially along the length of the tubular structure 12 and are coupled to one another by means of tie bars 16, well known in the art. In this example, the stent rings 14 are formed of a plurality of strut sections 18 arranged a zigzag shape. At the end of the stent 10 there may be provided radiopaque markers 20, again of a type well known in the art.

The stent 10 may be self-expanding or balloon expandable and made of any suitable material, of which many are known in the art.

Figure 2:
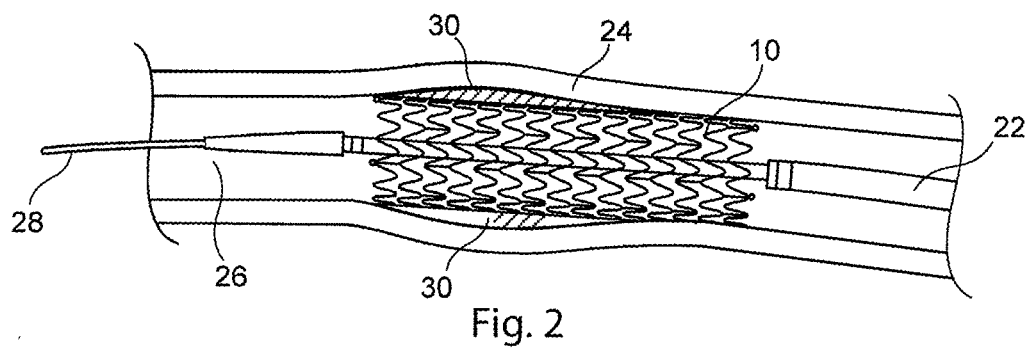
FIG. 2 is a schematic representation of the stent of FIG. 1 in the process of being deployed in a patient's vessel to treat a stenosis.

Referring also to FIG. 2, the stent 10 can be seen in the process of being deployed into a vessel 24, by means of an introducer assembly of which the distal end components 22 are visible in FIG. 2. These typically include a carrier element having a dilator tip 26 at the distal end thereof. The dilator tip 26 has a lumen therein for the passage of a guide wire 28. The components of the introducer assembly are not relevant to the teachings herein.

In the example in FIG. 2, the stent 10 is being deployed in order to treat a stenosis 30 of the vessel 24 and also to keep the vessel 24 open for the passage of blood therethrough.

Often, the deployment of a stent alone in the vessel does not provide a permanent solution as restenosis can often occur, closing the vessel again. This can be caused by a number of factors, including damage to the tissue of the vessel 24 during the vessel opening or angioplasty procedure, reoccurrence of the original causes of the stenosis, body reaction to the presence of a foreign body in the vessel, and so on.

Figure 3:
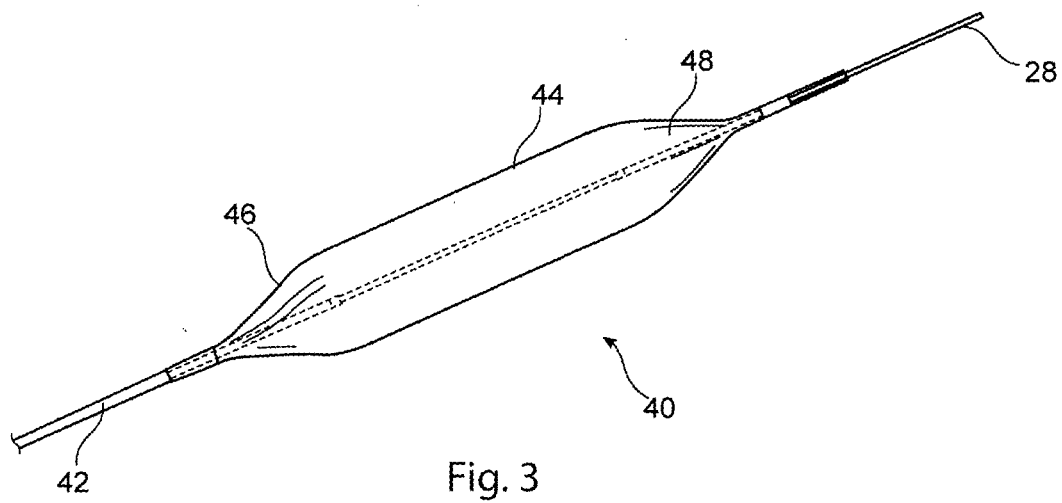
FIG. 3 is a side elevational view of an exemplary angioplasty balloon.

Referring now to FIG. 3, this shows an exemplary medical balloon 40 that may be used for angioplasty procedures, for deployment of a medical device such as a stent or stent graft, for valvuloplasty procedures or the like. The medial balloon is fitted to a balloon catheter 42 and has a substantially cylindrical balloon body 44 terminating in end cones 46, 48 that taper towards the balloon catheter 42 and fix the balloon wall to the catheter in fluid-tight manner. The balloon catheter 42 may include a lumen therein for the passage of a guide wire 28, as well as a lumen for providing inflation fluid into the balloon. The basic structure of the balloon 40 may be of a type conventional in the art, prior to modification by the teachings herein. Although FIG. 3 depicts a simple balloon structure, it may have any of the features known for such balloons, including a different shape, surface roughening, texturing and so on.

An angioplasty balloon of the type depicted schematically in FIG. 3 is often able to open a closed vessel in a very short period of time, for instance in seconds or minutes. While the initial vessel opening procedure is fast, there is a significant risk of future closure of the vessel, for instance by repeated collapse or restenosis. This can be caused by a number of factors including reactive hyperplasia resulting from the vessel opening procedure. Vessel closure can occur again within a few weeks or months of the medical procedure.

In the examples described briefly above in connection with FIGS. 2 and 3, it has been found that the administration of suitable bioactive agents into the vessel wall from the stent and/or from the medical balloon can substantially retard or prevent subsequent closure of the vessel due to restenosis. A variety of bioactive agents suitable for such purposes are known in the art including, for instance, antithrombogenic agents, thrombin inhibitors, tissue plasminogen activators, thrombolytic agents, fibrinolytic agents, vasospasm inhibitors, antiplatelet agents, antiproliferative agents and so on. A particularly effective bioactive agent known in the art is paclitaxel, other examples include dexamethasone, rapamycin, analogues of rapamycin such as Sirolimus, heparin and numerous other agents and compounds and analogues thereof. A list of suitable bioactive agents is given at the end of this specification, though it is to be understood that the list is not exhaustive.

The bioactive material is coated onto the medical device, for example the stent 10 of FIG. 1 or the balloon 40 of FIG. 3, so as to be released from the medical device into the tissues of the vessel 24, and should be dispensed at a rate suitable for treating the required medical condition. In the case of a stent or other implantable medical device, it may be desirable for the bioactive material to be released over a prolonged period of time, for example weeks or months. In the case of a medical device which is temporarily deployed in a patient's vessel, such as an angioplasty balloon or a device deployment balloon, the bioactive agent must typically be released from the balloon in a very short period of time, for instance within seconds or minutes, although sometimes up to an hour or more.

It is advantageous that the bioactive agent is held onto the medical device during deployment of the device in the patient without excessive loss of bioactive material into the patient's bloodstream, for instance. For this purpose, the prior art has suggested restraining the bioactive material, for instance in a containment or time release layer or matrix. Examples include: porous polymer layers into which bioactive material can be embedded, enclosed chambers holding the bioactive material, outer coatings disposed over the bioactive material and which dissolve or open during the deployment process, encapsulation of the bioactive material in micelles, capsules or pellets, and so on. Such containment measures can, however, lead to a number of disadvantages, including undesirable delayed administration of the bioactive material into body tissues, presence of a foreign substance in the body, possible onset of stenosis caused by the carrier device itself, and so on.

The inventors have found that the optimal solution is to apply the bioactive agent in the absence of any containment or time release substance and from a layer that is predominantly or entirely made of bioactive agents. In this manner, after administration of the bioactive agent or agents, the medical device remains free of agent delivery substances (polymer layers, for example) and no unnecessary carrier substances are released into the patient's body. A difficulty, however, has existed with getting the bioactive agent(s) to be held sufficiently well on the medical device.

The inventors have discovered that certain treatments of the medical device, and in particular the surface or surfaces of the device intended to be coated with one or more bioactive agents, can substantially increase the adhesion of the bioactive agent to the medical device before and during deployment of the medical device in the patient. Specifically, and as described in detail below, the inventors have discovered that functionalising the surface of the medical device to be coated by way of carboxylic acidification can substantially increase the adhesive characteristics of the surface, to such an extent that it is not necessary to use other mechanisms to retain the bioactive agent on the device. They have also discovered, as demonstrated below, that this functionalisation can allow significantly more bioactive agent to be carried on the medical device.

The term functionalisation as used herein denotes the treatment of the or one or more surfaces of the medical device with a carboxylic acid to cause a change in the characteristics of the surface. Functionalisation deposits onto the surface or surfaces acid species, which bind to the device surface and provide a bonding site for the bioactive material. In many cases the carboxylic acid species is deposited as individual molecules. They do not form a polymer matrix, for instance. Bonding of the bioactive agent is by means of covalent forces, in which base/acid combinations may form a Lewis adduct. Bioactive material molecules that overlie those directly attached to their covalent species will bind to other bioactive material molecules by same species covalent bonds.

In practice, the functionalisation leads to an increase in the polar acid component of the surface or surfaces, which leads to a significant increase in the quality of adhesion of bioactive agent to the contact surface of the medical device also to a substantial improvement in uniformity of coating across the contact surface(s) of the medical device.

The functionalisation process does not remove the oxide layer on the contact surface or surfaces, but attaches carboxylic acidic components to the oxide layer. The attached carboxylic acidic components could be described as becoming part of the oxide layer. Leaving the oxide intact maintains the stability of the treated surfaces of the medical device while altering the bonding properties of the oxide layer.

Significant improvement in bioactive material retention is experienced by functionalisation alone. Better retention is achieved, though, by first cleaning the contact surface or surfaces of the medical device to remove impurities, generally acquired during and after the manufacturing process. This can substantially increase the amount of carbon functional groups on the contact surface(s) of the medical device, leading to an even more uniform coating of bioactive material across the contact surface of the medical device.

Functionalisation by acidification may be carried out by a relatively strong acid, for instance having a pH of around 1.5, although tests have shown that a large range of acids in a large pH range can be effective.

The applicant's earlier patent applications EP-3,192,534 and EP-18275095.0 disclose methods of coating a medical device by prior functionalisation by acidification or basification of the base structure of the device. The teachings in these earlier patent applications have been found to provide good adhesion of a bioactive agent while avoiding the need for any containment mechanism to hold the bioactive agent. While these earlier methods are generally effective, the inventors have now discovered that a better and more a consistent coating or layer of bioactive agent can be applied to the medical device by a modified application procedure, described in detail below.

The examples described below relate to functionalisation by acidification. Citric acid is used as an example material for this functionalisation. Citrate could also be used, which acts as an acid as a result of its amphoteric properties. Other suitable carboxylic acids include acetic acid, lactic acid, adipic acid, alginic acid, tannic acid, oxalic acid, formic acid, levulinic acid, hyaluronic acid, acrylic acid, propionic acid, hydroxamic acid and other conjugates and derivatives. Tests have also been performed using ascorbic acid and found to be advantageous. Other carboxylic acids that may be used include: methanoic acid (formic acid), ethanoic acid (acetic acid), ethanedioc acid (oxalic acid), oxoethanoic acid (glyoxylic acid), 2-hydroxyethanoic acid (glycolic acid), propanoic acid (propionic acid, ethanecarboxylic acid), prop-2-enoic acid (acrylic acid, acroleic acid, ethylenecarboxylic acid, propene acid, vinylformic acid), propanedioic acid (malonic acid, methanedicarboxylic acid), 2-oxopropanoic acid (pyruvic acid, α-ketopropionic acid, acetylformic acid, pyroracemic acid), 2-hydroxypropanoic acid (lactic acid, milk acid), butanoic acid (butyric acid, propanecarboxylic acid), 2-methylpropanoic acid (isobutyric acid, isobutanoic acid), butanedioic acid (succinic acid), 3-oxobutanoic acid (acetoacetic acid), (E)-butenedioic acid (fumaric acid, trans-1,2-ethylenedicarboxylic acid, 2-butenedioic acid, trans-butenedioic acid, allomaleic acid, boletic acid, donitic acid, lichenic acid), (Z)-butenedioic acid (maleic acid, cis-butenedioic acid, maleinic acid, toxilic acid), oxobutanedioic acid (oxaloacetic acid, oxalacetic acid, oxosuccinic acid), hydroxybutanedioic acid (malic acid, hydroxybutanedioic acid), 2,3-dihydroxybutanedioic acid (tartaric acid, 2,3-dihydroxysuccinic acid, threaric acid, racemic acid, uvic acid, paratartaric acid), (E)-but-2-enoic acid (crotonic acid, trans-2-butenoic acid, beta-methylacrylic acid, 3-methylacrylic acid, (E)-2-butenoic acid), pentanoic acid (valeric acid, valerianic acid, butane-1-carboxylic acid), pentanedioic acid (glutaric acid, propane-1, 3-dicarboxylic acid, 1,3-propanedicarboxylic acid, n-pyrotartaric acid), 2-ketoglutaric acid (alpha-Ketoglutaric acid, 2-ketoglutaric acid, α-ketoglutaric acid, 2-oxoglutaric acid, oxoglutaric acid), hexanoic acid (caproic acid, n-caproic acid), hexanedioic acid (adipic acid, hexane-1,6-dioic acid), 2-hydroxypropane-1,2,3-tricarboxylic acid (citric acid, 3-carboxy-3-hydroxypentanedioic acid, 2-hydroxy-1,2,3-propanetricarboxylic acid), prop-1-ene-1,2,3-tricarboxylic acid (aconitic acid, achilleic acid, equisetic acid, citridinic acid, pyrocitric acid), 1-hydroxpropane-1,2,3-tricarboxylic acid (isocitric acid), (2E,4E)-hexa-2,4-dienoic acid (sorbic acid), heptanoic acid (enanthic acid, oenanthic acid, n-Heptylic acid, n-Heptoic acid), heptanedioic acid (pimelic acid), cyclohexanecarboxylic acid, benzenecarboxylic acid ("benzoic acid, carboxybenzene, dracylic acid), 2-hydroxybenzoic acid (salicylic acid), octanoic acid (caprylic acid), benzene-1,2-dicarboxylic acid (phthalic acid), nonanoic acid (pelargonic acid, 1-octanecarboxylic acid), benzene-1,3,5-tricarboxylic acid (trimesic acid), (E)-3-phenylprop-2-enoic acid (cinnamic acid, trans-cinnamic acid, phenylacrylic acid, cinnamylic acid, 3-phenylacrylic acid, (E)-cinnamic acid, benzenepropenoic acid, isocinnamic acid), decanoic acid (capric acid, decanoic acid), decanedioic acid (sebacic acid 1,8-octanedicarboxylic acid), undecanoic acid (hendecanoic acid), dodecanoic acid (lauric acid, dodecylic acid, dodecoic acid, laurostearic acid, fulvic acid, 1-undecanecarboxylic acid, duodecylic acid), benzene-1,2,3,4,5,6-hexacarboxylic acid (mellitic acid, graphitic acid, benzenehexacarboxylic acid), tridecanoic acid (tridecylic acid), tetradecanoic acid (myristic acid), pentadecanoic acid (pentadecylic acid), hexadecanoic acid (palmitic acid), heptadecanoic acid (margaric acid, heptadecylic acid), octadecanoic acid (stearic acid), (9Z)-octadec-9-enoic acid (oleic acid, (9Z)-octadecenoic acid, (Z)-octadec-9-enoic acid, cis-9-octadecenoic acid, cis-Δ9-octadecenoic acid, (9Z,12Z)-octadeca-9,12-dienoic acid (linoleic acid), (9Z,12Z,15Z)-octadeca-9,12,15-trienoic acid (ALA, α-linolenic acid, cis, cis,cis-9,12,15-octadecatrienoic acid, (Z,Z,Z)-9,12,15-octadecatrienoic acid), (6Z, 9Z,12Z)-octadeca-6,9,12-trienoic acid (GLA, γ-linolenic acid, gamolenic acid), (6Z,9Z,12Z,15Z)-octadeca-6,9,12, 15-tetraenoic acid (SDA, stearidonic acid, moroctic acid), nonadecanoic acid (nonadecylic acid), eicosanoic acid (arachidic acid, eicosanoic acid, arachic acid), (5Z,8Z,11Z)-eicosa-5,8,11-trienoic acid (ead's acid), "(5Z,8Z,11Z,14Z)-eicosa-5,8,11,14-tetraenoic acid (AA, ARA, arachidonic acid), henicosanoic acid, docosanoic acid (behenic acid), (4Z,7Z,10Z,13Z,16Z,19Z)-docosa-4,7,10,13,16,19-hexaenoic acid (DHA, cervonic acid), tricosanoic acid (tricosylic acid), tetracosanoic acid (lignoceric acid), pentacosanoic acid (pentacosylic acid), and hexacosanoic acid (cerotic acid). These acids may be used singly or in combination with one another as a mix of two or more of the above-mentioned carboxylic acids.

The skilled person will recognise from the teachings herein that a large range of acids can be used to achieve the same effects. It will be apparent that conjugates and derivatives may be equally suitable for such purposes. As an example only, hydroxamic acid is a suitable derivate of carboxylic acid.

The specific embodiments described below are directed to a stent formed of nickel titanium alloy (for instance Nitinol) which is functionalised and then coated with paclitaxel, a preferred bioactive agent, either in pure form or mixed or combined with one or more additional bioactive agents and with or without an excipient. The skilled person will appreciate that this is an example only and that the teachings herein are applicable to the other stent materials, including metals, metal alloys and also polymer based stents. The teachings herein are not limited to stents only and can be applied to other medical devices including balloons.

Figure 4:
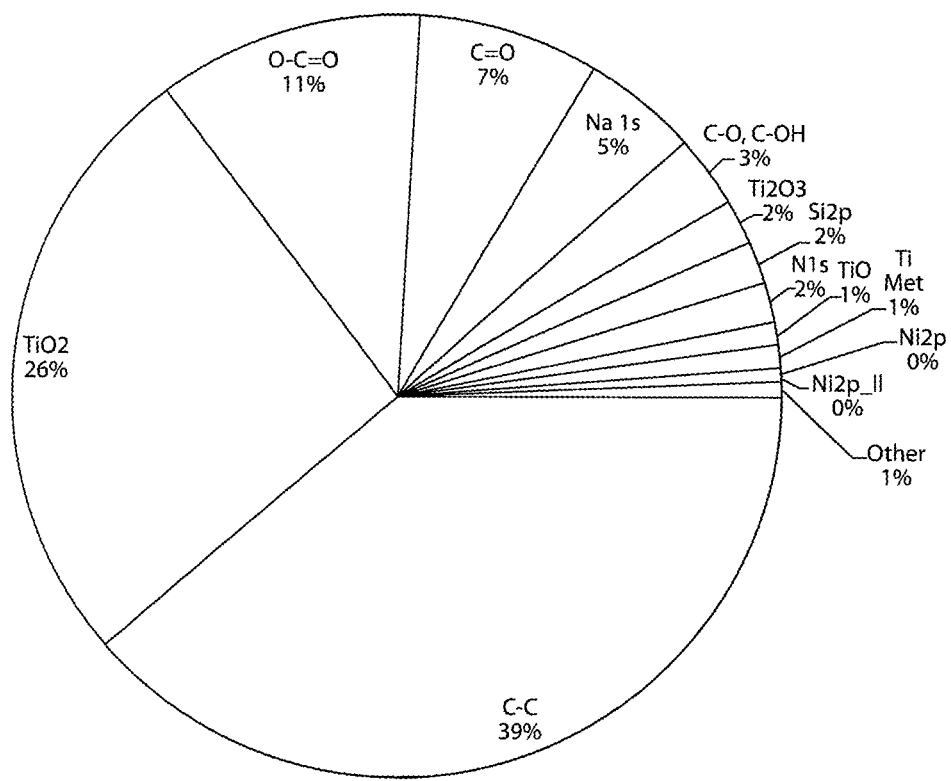
FIG. 4 is a chart depicting the constitution of a cleaned non-functionalised contact surface of a Nitinol stent.

Referring now to FIG. 4, this shows the constitution of a contact surface of a Nitinol stent, measured by x-ray photoelectron spectroscopy (XPS) following functionalisation of the surface with citric acid. As explained above, this functionalisation deposits onto the device surface acidic species which change the adhesive characteristics of the surface. As can be seen from FIG. 4, the treated contact surface exhibits a high percentage of carbon-to-carbon (C—C) components, a high proportion of titanium dioxide and also other components including O—C=O, C=O and other carbon and oxygen components.

Functionalisation by acidification substantially reduces the amount of nickel at the contact surface, which the inventors have discovered adversely affects the retention of bioactive agents on the contact surface.

The acidic species and the titanium dioxide on the treated contact surface increase the acidic polar component of the surface energy of the contact surface of the medical device, providing good adhesion characteristics to the surface, for holding a bioactive agent (being the conjugate base) onto the contact surface of the medical device. This is substantially better than what can be achieved with a non-functionalised contact surface of a medical device. Furthermore, this process of functionalisation by acidification increases the reliability of the coating process such that a more consistent dosage of bioactive agent is applied on the contact surface during batch coating.

Even though it has been found that functionalisation by acidification only provides a notable increase in adhesion of a bioactive agent onto the medical device, it has been found that cleansing of the contact surface or surfaces of the medical device prior to acidification results in even better bioactive material retention on the medical device.

Cleaning with an alcohol such as ethanol, can remove larger impurities from the contact surface. As is described in further detail below, the preferred embodiments functionalise the contact surface or surfaces of the stent after such cleaning.

In the earlier methods disclosed in the applicant's abovementioned patent applications, the medical device was also plasma cleaned, which creates an atomically cleaned surface, removing in particular carbon components that may have adhered to the contact surface during or after manufacture. The plasma treatment is preferably relatively low energy so as not to remove the oxide layer on the outer surface(s) of the medical device.

Suitable plasma machines include the Gatan Solarus Model 950 and Diener Femto type B. An example of an appropriate plasma cleaning treatment, for an $H_2O_2$ plasma, has the following characteristics:

Vacuum=509-531 mTorr
Turbo Pump=750 Hz, 1.0 A
$H_2$ flow=6.3-6.4 sccm
$O_2$ flow=27.4-27.5 sccm
Power=50 W
Operating frequency: 13.56 MHz
Treatment time=5 minutes.

Plasma pre-treatment results in the generation of an even greater extent of functionalised carbon bond species at the contact surface of the medical device during the process of acidification. The amount of titanium dioxide at the contact surface is substantially reduced compared to the case of functionalisation only (FIG. 4). The predominant acidic species of the contact surface are, in this example:

O—C=O, C—O, C—OH and C=O. These species provide an acid polar element to the surface energy of the contact surface(s) of the medical device and one which is very stable across the entire extent of the contact surface. However, plasma cleaning is not essential and in at least some embodiments, as in the preferred embodiments described below, is not carried out. It has been found, particularly for the process described herein, that the increase in surface energy produced at the treated surfaces as a result of plasma cleaning is not needed.

Figure 5:
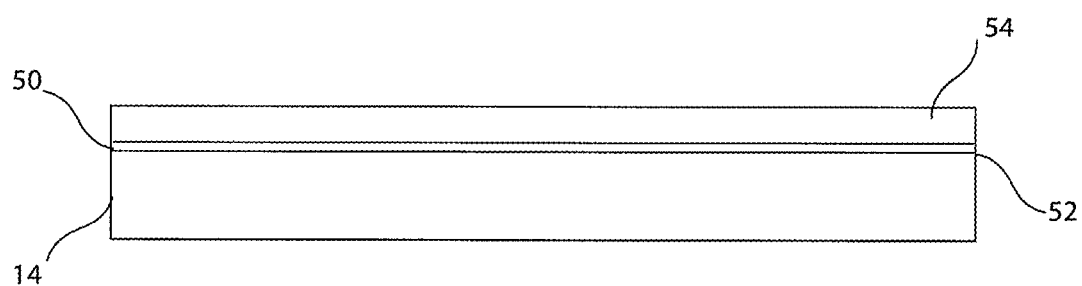
FIG. 5 is a schematic diagram of a transverse cross-sectional view of a stent strut of the stent of FIGS. 1 and 2 to show the functionalised contact surface and bioactive material coating.

Referring briefly to FIG. 5, this shows a transverse cross-sectional view of a stent, such as the stent 10 shown in FIG. 1. The tubular structure 12 of the stent, in particular strut 14, thereof has had its contact surface 50 functionalised by acidification so as to form a functionalised contact surface 52 with the characteristics shown for example in FIG. 4. A bioactive agent layer 54 is deposited onto the functionalised contact surface 52 (for example by spraying, rolling or dipping). It is not necessary to embed the bioactive agent in any containment matrix or layer, as is necessary with the prior art. It is preferred that the bioactive agent layer 54 is distinct from the base support (formed of the structure 14 and functionalised surface 52). Thus, the exposed surface of the bioactive agent layer 54 is solely bioactive agent or material, potentially with additional functional groups such as excipients.

There follows a description of preferred embodiments for coating a stent with a preferred bioactive material, in this case paclitaxel. The preferred embodiment functionalises at least one contact surface of the stent with citric acid applied to the contact surface(s) and thereafter a layer of paclitaxel, in the described embodiments dihydrate paclitaxel. This forms a structure with what could be described as three distinct layers as a minimum. The first layer is the base layer, being the structure of the stent, for example the Nitinol base (and it is to be understood that there will be a naturally formed oxide layer at the exposed surfaces). The second layer is a functionalisation layer of citric acid and overlying this is a third layer of dihydrate paclitaxel. The paclitaxel may be in pure form but it is not excluded that it may include other bioactive agents and in some embodiments, particularly when the device is a balloon, an excipient such as urea. The layer of bioactive material does not include any containment or time release mechanism, such as a polymer holding matrix or overlying containment device. In practice, therefore, the layer of bioactive agent constitutes the outermost layer of the device, although it is not excluded that there may be additional bioactive materials lying thereover but such that once those additional layers have been dissolved or otherwise absorbed into the patient, the layer of paclitaxel (or other bioactive agent) becomes the effective outermost layer and in a form that is not contained or otherwise restrained by any other compound or mechanism.

It has been found that in a conventional carboxylic acid deposition processes, the layer of carboxylic acid may typically be around 100 nanometres or more in thickness. Whilst such a layer can provide a good adhesion site for a variety of bioactive agents such as paclitaxel, the inventors have discovered that such an amount of carboxylic acid can be excessive and desorb in situ, causing particulate loss of bioactive material adhered to the carboxylic acid layer. The inventors have discovered that a reduction in the amount of carboxylic acid on the contact surface of the medical device does not lead to a material loss of adhesion of bioactive agent to the medical device and that only a very thin coating is required. For example, a single layer of carboxylic acid molecules need be adhered to the contact surface of the medical device and it is not necessary to have a thicker coating in which carboxylic acid molecules are bonded to one another. In tests, the inventors have discovered that forming as thin as possible a layer of carboxylic acid on the contact surface of the medical device can result in a significantly more even and complete layer of bioactive agent over the area of the contact surface or surfaces and one that holds better to the medical device when in situ.

The process described below applies carboxylic acid to the contact surface or surfaces of the medical device and then subjects the medical device (or at least the contact surface or surfaces) to a washing process to take off excess carboxylic acid. It has been found that the washing process does not completely remove the carboxylic acid from the contact surface or surfaces of the medical device but leaves a minimal layer of carboxylic acid, used for adhering a bioactive material layer thereto.

Figure 6:
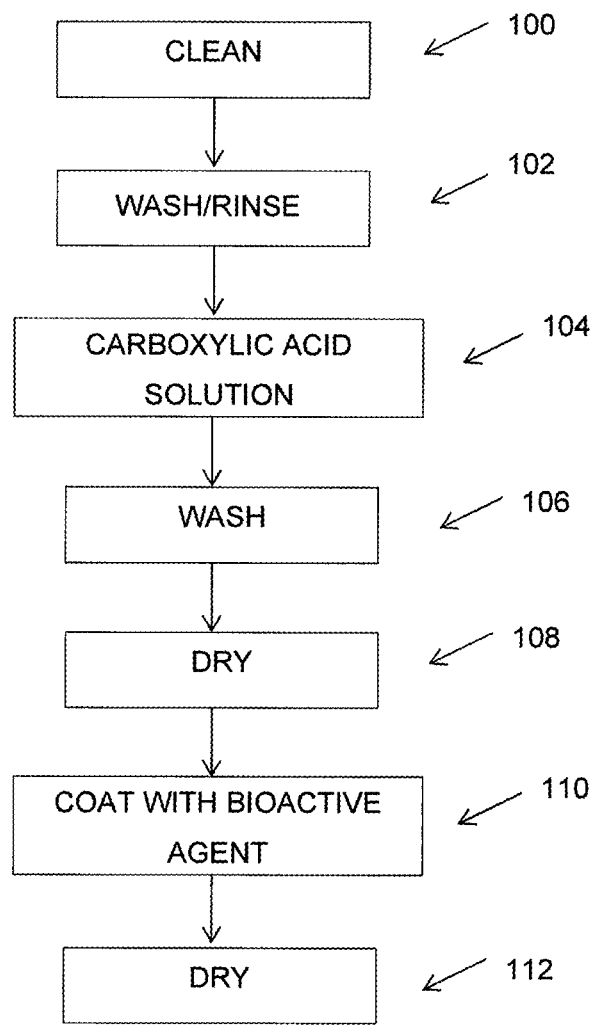
FIG. 6 is a flow chart of the preferred stent preparation and coating method.

FIG. 6 shows a preferred embodiment of method of coating a medical device according to the teachings herein. In this embodiment, the medical device is a nickel titanium alloy stent, functionalised with citric acid and then coated with a layer of bioactive material comprising or consisting of paclitaxel. The skilled person will appreciate that this method can readily be used or modified to coat other medical devices, including balloons and any of the other medical devices referred to herein, and that the bioactive agent can be any of those referred to herein.

In step 100 the medical device is cleaned, in this embodiment by dipping the device in a solution of sodium hydroxide (NaOH) at a concentration of 0.1 grams of NaOH in 100 ml of water. The pH of the solution with the stent added was around 12.65. The cleaning step left the stent in solution for 30 minutes or so. This cleaning/soaking stage could be shorter or longer than 30 minutes, although it has been found that 30 minutes is optimal. This stage 100 could be termed pre-functionalisation cleaning.

Following the cleaning stage 100, the stent was rinsed, at step 102, in water in order to rinse off any residual citric hydroxide on the stent surfaces. It has been found that ten rinsing passes provide optimal rinsing. The washed and rinsed stent was then transferred immediately to a carboxylic acid solution, at step 104, in order to functionalise the surfaces of the stent. In a preferred embodiment, transfer to the carboxylic acid solution is effected without drying following rinsing.

As indicated above, the preferred carboxylic acid used in this example is citric acid. This is preferably a 5% citric acid solution (that is 5 grams in 100 ml of water), having a pH of around 1.8. The stent was retained in the citric acid solution for around 2 hours at a temperature of around 30° C. The skilled person will appreciate that the concentration of carboxylic acid, the dipping time and the temperature may be varied and the parameters given are by way of example only.

Following the carboxylic acid functionalisation step 104, the stents was washed, at step 106, preferably in water in a process involving five to twenty, in the preferred embodiment, ten rinse passes. Rinsing can also be carried out by moving the stent in water for a period, preferably at least 5 seconds up to one hour. This may be by dipping the stent in a bath and moving or by placing the stent in a flow of water for these time periods. In the preferred embodiment, the surfaces of the stent after the final rinse were found to have in the region of pH7. This washing/rinsing step could be described as a post-functionalisation washing step.

After washing/rinsing, the stent was allowed to dry at step 108. This may be in air or in a clean environment. After drying, at step 110, the contact surface or surfaces of the stent was coated with a bioactive agent, in this example with a dihydrate paclitaxel. This coating step may be by spraying, dipping, rolling, plasma deposition or any other suitable method.

As appropriate, the stent may be dried (step 112) after coating with the bioactive agent.

While in this example the stent was cleaned with sodium hydroxide, other suitable cleaning solutions include: ethanol and mixtures of ethanol with water, isopropanol (IPA) and mixtures with water, acetone, acetonitrile, hydrogen peroxide, sodium hypochlorite, a surfactant or boiling water.

It has been found that as the carboxylic acid can be applied within wet chemical process, plasma cleaning is not necessary in the preferred embodiments.

The skilled person will appreciate that the method of FIG. 6, and indeed any method in accordance with the teachings herein, could treat a plurality of stents simultaneously or sequentially in batch manner. Furthermore, the process could be applied to the entirety of the stent, so as to treat every exposed surface of the stent, or could be performed only on the surface or surfaces intended to be coated with bioactive agent, for instance the luminal or the abluminal sides of the stent.

Figure 7:
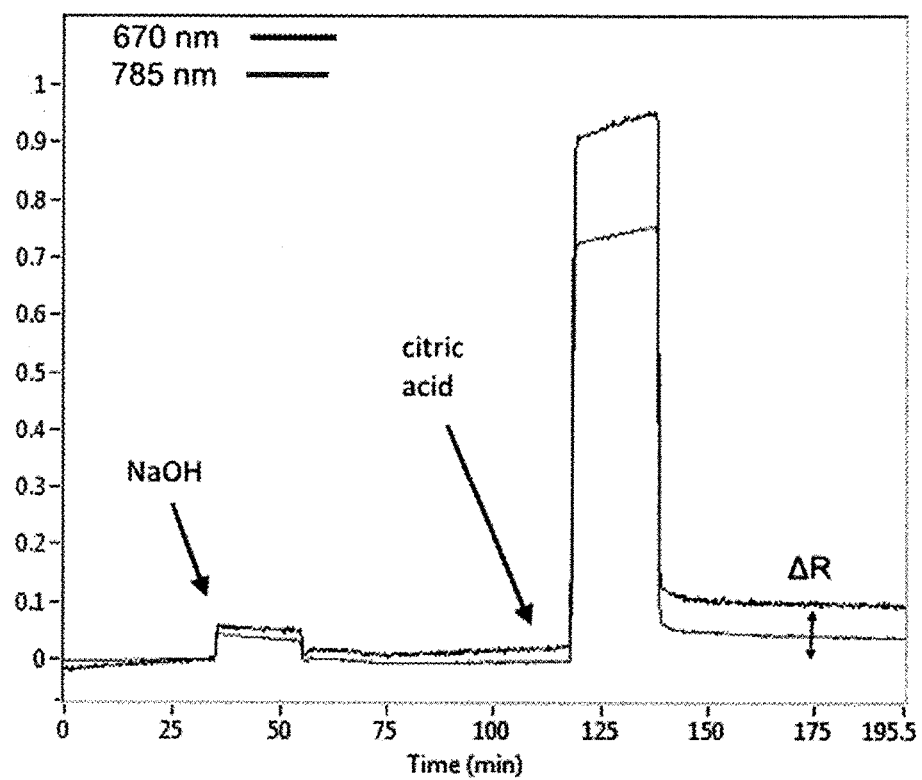
FIG. 7 is a graph showing the coating effect of the method of FIG. 6.

FIG. 7 is a graph showing the effect of the washing and functionalisation steps of the embodiment of method shown in FIG. 6. The measurements were obtained by Multi-parametric surface plasmon resonance (MP-SPR), taken at two different laser wavelengths as shown. The cleaning stage with NaOH and the functionalisation stage with citric acid were interposed with water washing stages in accordance with the described method. As can be seen, sodium hydroxide cleaning only produced a minor and temporary layer of the washed medical device surface, which was then washed off during the subsequent washing step. Coating with citric acid produced a notable layer, most but not all was removed during the subsequent water washing/rinsing stage. Even after significant water washing, there remained a coating of citric acid, depicted by the thickness measurement $\Delta R$ in the graph. Water washing removed excess citric acid very quickly, it is believed within around 5 seconds, although the washing step could be continued for a plurality of rinse cycles or for a significant time as described elsewhere in this patent specification. It has been found that the citric acid layer after washing and drying is in the region of 0.4 to 10 up to 22 nanometres, in most cases just one molecule thick.

Figure 8:
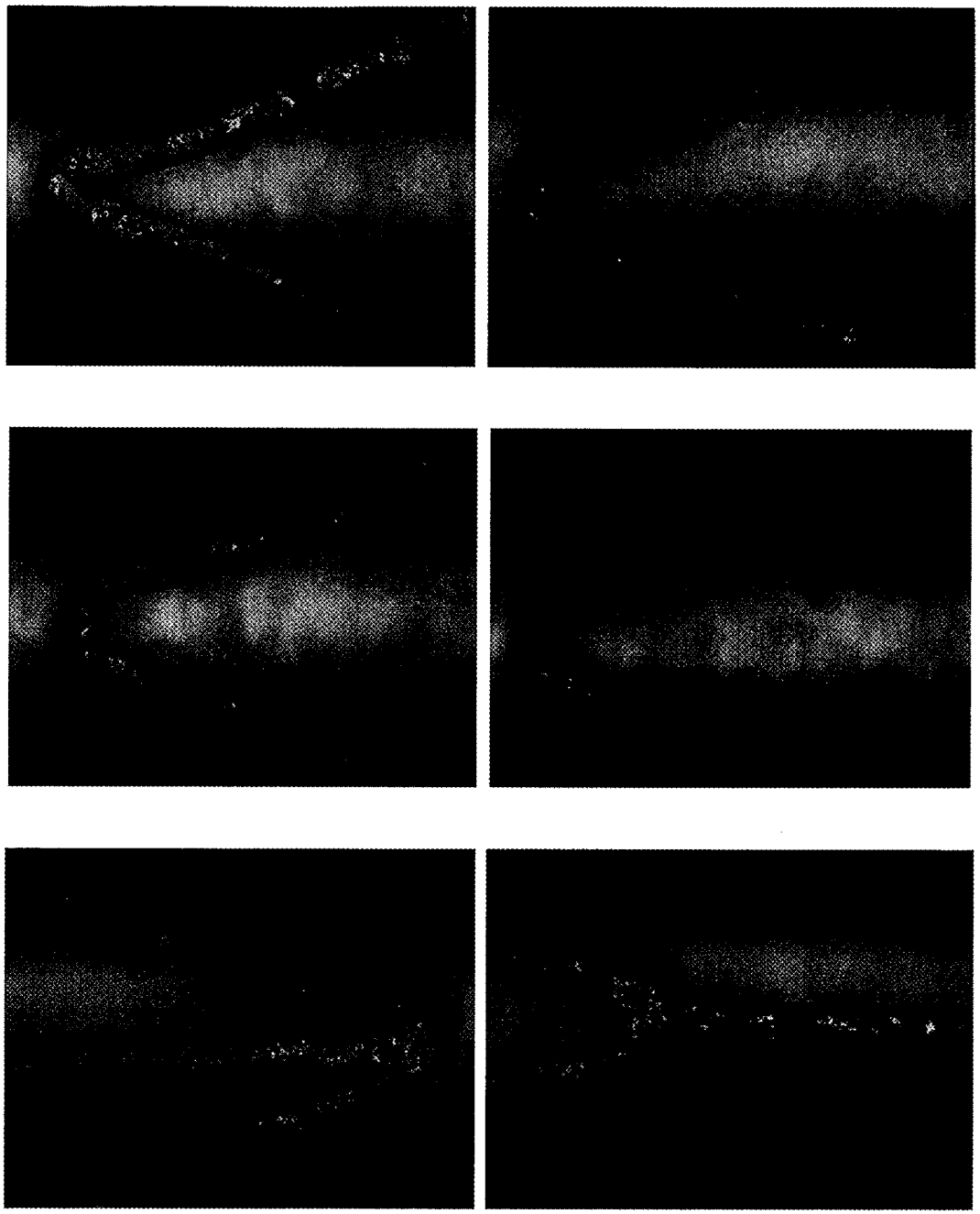
FIG. 8 is a series of photographs showing the coating of a stent by the preferred method.

With reference now to FIG. 8, this is series of photographs showing the results of coating of a stent using the method of FIG. 6, particularly subjecting a stent to: (a) a pre-functionalisation wash in sodium hydroxide, (b) followed by a citric acid functionalisation, (c) followed by a washing stage to remove excess citric acid, and (d) followed by a step of coating the stent surfaces with dihydrate PTX. As can be seen at FIG. 8, this process can produce a generally uniform and consistent coating of paclitaxel over the stent surfaces. In fact, the coating is notably more uniform than in the prior art.

Figure 9:
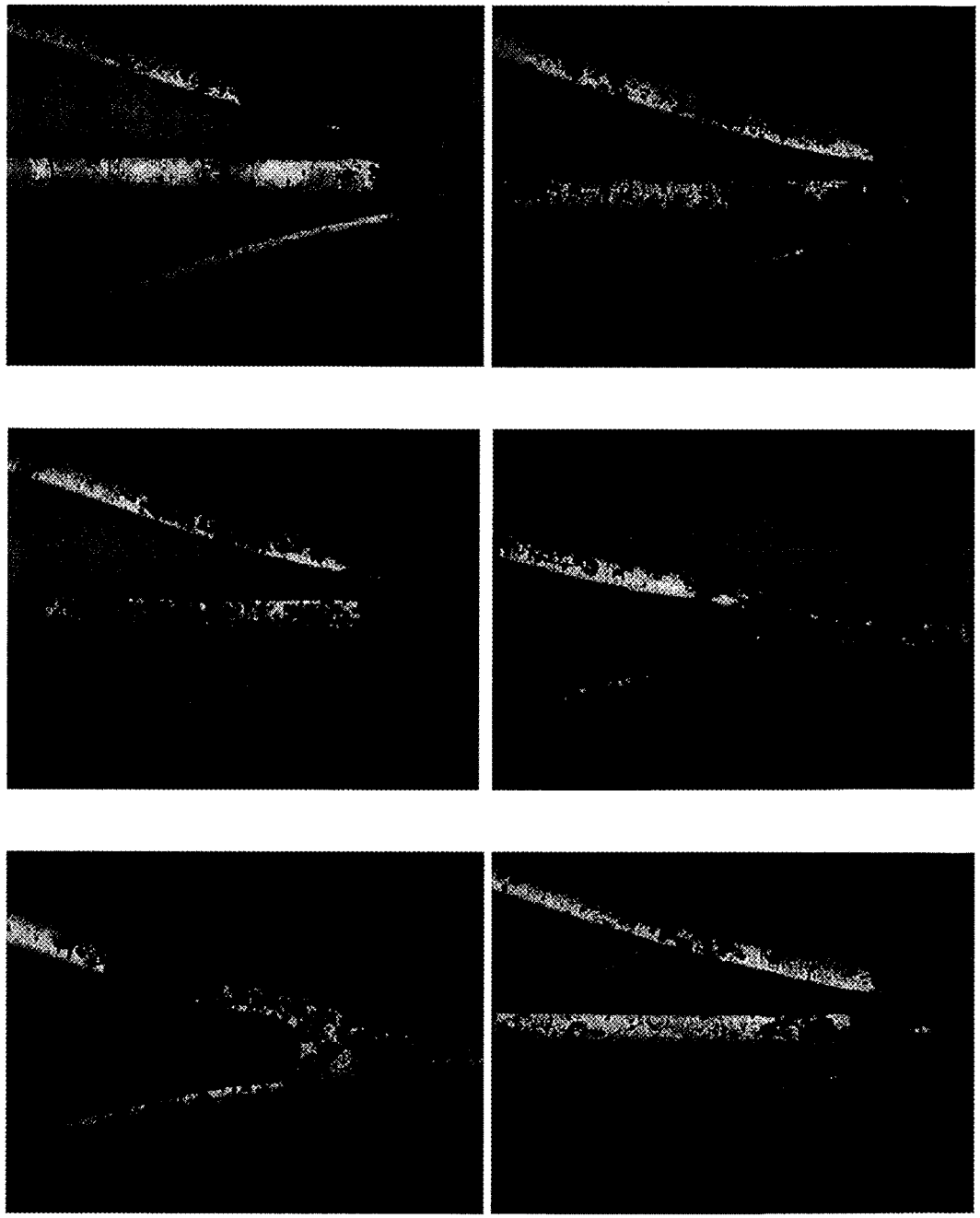
FIG. 9 is a series of photographs showing a stent that has been plasma cleaned and then coated with paclitaxel.
Figure 10:
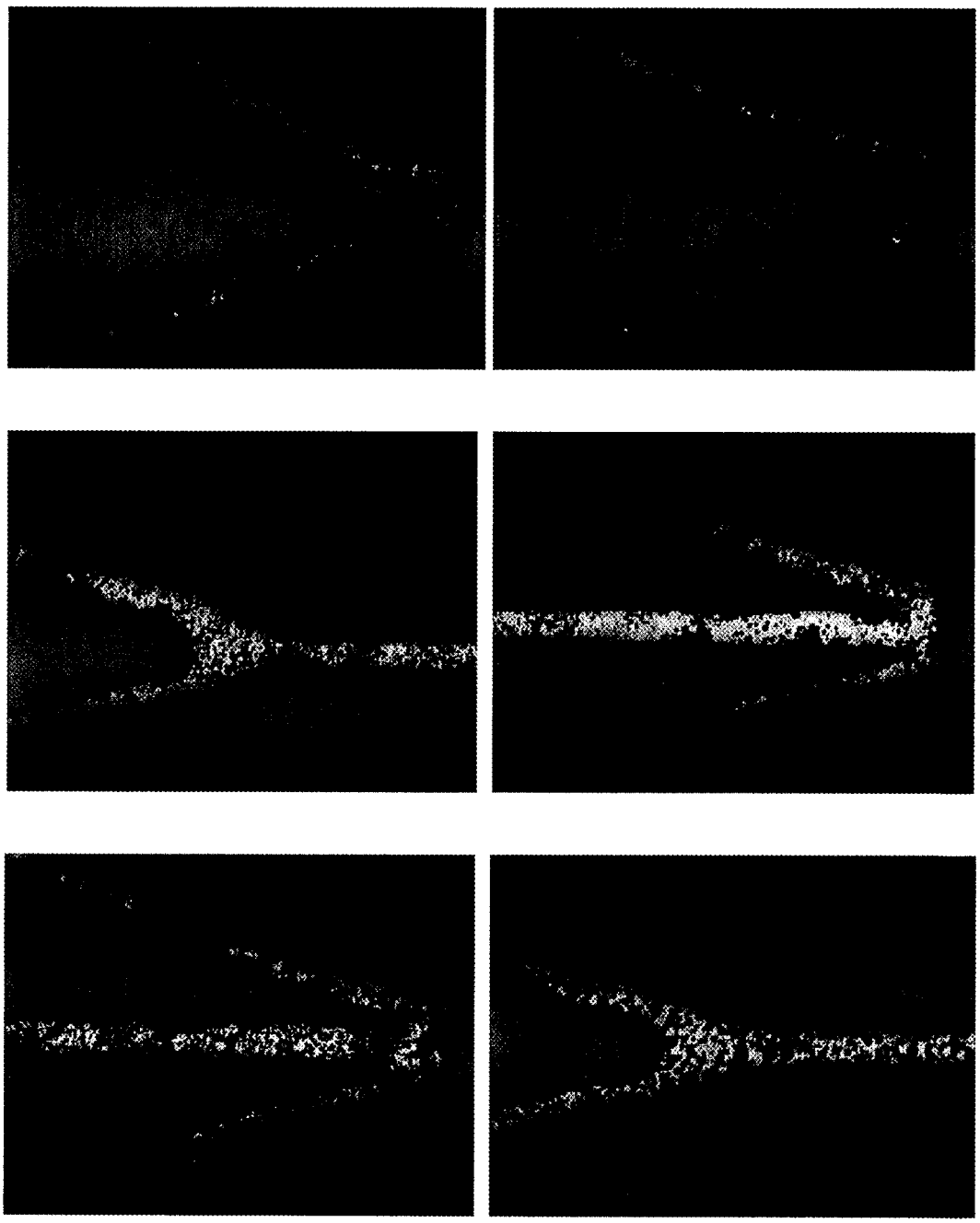
FIG. 10 is a series of photographs of a stent that has been plasma cleaned, functionalised with citric acid and then coated with bioactive agent.

The coating of FIG. 8 can be contrasted with that of FIG. 9, which is a series of photographs of a stent washed in ethanol only and then having had applied thereto a coating of dihydrate paclitaxel. As can be seen in the photographs of FIG. 9, the coating is incomplete and non-uniform. Similarly, referring to FIG. 10, this shows a series of photographs in which a stent was coated by first plasma cleaning the stent, followed by dipping the stent in a citric acid solution, washing the stent and then applying a coating of dihydrate paclitaxel. While the coating is notably better than without the use of citric acid functionalisation, as shown in the example of FIG. 8, it has been found, as described above, that if too much carboxylic acid is present, this can desorb in use, removing paclitaxel (PTX) particulate with it and resulting in a coating that is non-uniform across the contact surfaces of the stent.

Although the method and system described above and in conjunction with coating of a stent, the same method and system can be used to coat other medical devices, including medical balloons.

In the case of medical balloons and other short term use medical devices, it is generally preferred that the bioactive agent is released quickly into the patient's tissue. For this purpose, an excipient such as urea and/or urea derivatives, gallates and gallate derivatives (such as epi gallo catechin gallate), saccharides and/or saccharide derivatives, chitin and/or chitin derivatives, ascorbic acid, citric acid, sterates and/or sterate derivatives, polyvinyl pyrolidone, dicalcium phosphate dihydrate, eudragit polymers and/or eudragit polymers derivatives, cellulose and/or cellulose derivatives, PEG, poylsorbate 80, sodium lauryl sulphate, chitosan, magnesium dioxide, silicon dioxide, carbonate derivatives, plasdone, butylated hydroxyanisole, succinic acid, sodium dioctyl sulfosuccinate, precirol ATO 5, may be added to the bioactive agent layer or disposed so as to underlie the bioactive material layer. The excipient will speed up the release of the bioactive agent once the medical device is deployed within the patient, for instance by the excipient dissolving within the patient's blood plasma and providing for quick release of the bioactive agent. This can be particularly useful in treating initial reactive hyperplasia occurring as a result of angioplasty or other medical procedures. Where an excipient is used, this may be as a sublayer between the layer of bioactive material and the medical device or as a layer above the layer of bioactive material. The excipient acts to speed the release of the bioactive agent (drug for example), compared to a drug per se or a drug held in a containment or time release layer. In the case of a sublayer of excipient, the functionalisation of the surface to be coated will be matched to the nature of the excipient and the excipient matched to the bioactive agent or agents.

The bioactive material can be any of a large variety and many bioactive materials for coating medical devices are known in the art. The layer of bioactive material applied to the functionalised surfaces of the device may be of a single bioactive material or a combination of different bioactive agents, in dependence upon the desired treatment. There may also be provided other active agents in the bioactive material layer, such as excipients or other release facilitators.

The bioactive material of the coating may include at least one of: paclitaxel and/or paclitaxel derivatives, rapamycin and/or rapamycin derivatives, docetaxel and/or docetaxel derivatives, cabazitaxel and/or cabazitaxel derivatives, taxane and/or taxane derivatives, estrogen or estrogen derivatives; heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine or another antiplatelet agent; colchicine or another antimitotic, or another microtubule inhibitor; cytochalasin or another actin inhibitor; a remodelling inhibitor; deoxyribonucleic acid, an antisense nucleotide or another agent for molecular genetic intervention; GPIIb/IIIa, GP Ib-IX or another inhibitor or surface glycoprotein receptor; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; 60Co (having a half-life of 5.3 years), 192Ir (73.8 days), 32P (14.3 days), 111In (68 hours), 10 90Y (64 hours), 99mTc (6 hours) or another radio therapeutic agent; iodine containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting 15 enzyme (ACE) inhibitor; ascorbic acid, alphatocopherol, superoxide dismutase, deferoxyamine, a 21-aminosteroid (lasaroid) or another free radical scavenger, iron chelator or antioxidant; angiopeptin; a 14C-, 3H-, 131I1-, 32P- or 36S-radiolabelled form or other radio labelled form of any of the foregoing; or a mixture of any of these.

The teachings herein have also been tried with tannic acid with significant benefits. Tannic acid molecules are relatively large and it has been found are particularly effective for binding bioactive agents, such as paclitaxel, to a medical device, achieving significant dosages of agent to the medical device. Tannic acid can also act as an excipient as it speeds the release of the bioactive agent once hydrolysed. Other tests have used with success: lactic acid, acetic acid, formic acid, ascorbic acid, acrylic acid, propionic acid, phosphonic acid and phosphoric acid.

The teachings herein make it possible to attach bioactive agents to the surfaces of medical devices without having to rely on binding agents or polymer of other matrix materials as in the prior art. Binding agents are considered to be substances which enhance the adhesion of a bioactive material layer at the support surface and generally act to retard the release of the bioactive agent or agents. A polymer or other matrix performs a similar role. Binding agents and matrices act as containment mechanisms.

As has been described above, the teachings herein can be applied to a variety of medical devices including, in addition to the examples already indicated, vascular filters, vascular plugs, coils, neural vascular devices, pacemakers, prostheses, surgical tools, catheters, and so on. The bioactive agent can also be agents for inflammation reduction, for reducing vascular spasm, prosthesis acceptance, bone and tissue growth promoters, and so on.

In one aspect, the taught medical device has a structure for implantation or disposition inside a patient, the structure including at least one coated surface, the at least one coated surface being carboxylic acid functionalised by a carboxylic acid layer of up to 2.2 nanometres in thickness and being coated with a bioactive agent layer directly on the at least one functionalised surface.

In this aspect, the bioactive agent layer is preferably one of:
  a) wholly or principally of bioactive material;
  b) wholly or partially a therapeutic substance;
  c) wholly or partially an anti-proliferative bioactive substance; and
  d) wholly or partially paclitaxel.

In this aspect, the bioactive agent layer is preferably free of one or more of:
  a) containment elements;
  b) binding agents; and
  c) time control release agents; and
  d) polymer or other matrix material.

In this aspect, the functionalised surface is preferably substantially impervious to the material coating.

In this aspect, the at least one surface is preferably functionalised with one or more of: citric acid, acetic acid, lactic acid, ascorbic acid, tannic acid, carboxylic acid, alginic acid, adipic acid, hyaluronic acid and conjugates and derivatives thereof.

In this aspect, the medical device preferably is or includes:
  a) a stent or balloon;
  b) a stent and wherein the structure is made of nickel titanium alloy;
  c) a balloon and the coating includes an excipient.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

What is claimed is:

1. A method of coating a medical device having a structure for implantation or disposition inside a patient, the structure including at least one surface for coating, the method including the steps of:
    functionalising the at least one surface of the structure by subjecting the at least one surface to acidification by a carboxylic acid to form at least one acid functionalised surface; washing the at least one acid functionalised surface to provide an acid functionalised and cleaned surface, wherein said washing involves rinsing the at least one surface of the medical device in water, wherein said rinsing removes amounts of the carboxylic acid but not all of the carboxylic acid, and wherein said rinsing is conducted until a thickness of a layer of the carboxylic acid is reduced to a minimum thickness achievable by rinsing the at least one surface of the medical device in water and at the end of said rinsing the at least one acid functionalised and cleaned surface exhibits a neutral pH; and applying a bioactive agent layer directly on so as to overlie the at least one acid functionalised and cleaned surface.

2. A method according to claim 1, including a pre-functionalisation washing step of washing the medical device prior to the functionalising step.

3. A method according to claim 2, wherein the pre-functionalisation washing step washes the at least one surface of the medical device in a solution of sodium hydroxide.

4. A method according to claim 2, including a step of rinsing the at least one surface of the medical device subsequent to the pre-functionalisation washing step and prior to the functionalising step.

5. A method according to claim 4, wherein the at least one surface of the medical device is subjected to the functionalising step without drying after the pre-functionalisation washing step.

6. A method according to claim 1, wherein the functionalising step involves soaking the at least one surface of the medical device in the carboxylic acid.

7. A method according to claim 1, wherein the functionalising step involves soaking the at least one surface of the medical device in a citric acid solution.

8. A method according to claim 1, wherein the carboxylic acid is citric acid, and wherein the washing step is conducted sufficiently to provide a citric acid layer that has a thickness in the range of 0.4 to 22 nanometers when dried.

9. A method according to claim 1, wherein the washing step involves
rinsing in water 5 to 20 times; and/or
rinsing in moving water for a period of 5 seconds to one hour.

10. A method according to claim 1, wherein the bioactive agent layer comprises an anti-proliferative bioactive substance.

11. A method according to claim 1, wherein the bioactive agent layer is free from any polymer matrix that retards release of the bioactive agent.

12. A method according to claim 1, wherein the step of functionalising the at least one surface does not remove or alter oxide on the at least one surface.

13. A method according to claim 1, wherein the functionalising step includes treating the at least one surface with one or more of: citric acid, acetic acid, lactic acid, ascorbic acid, tannic acid, alginic acid, adipic acid, hyaluronic acid and conjugates and derivatives thereof.

14. A method according to claim 1, wherein the medical device is or includes a stent or balloon.

15. A method of coating a medical device having a structure for implantation or disposition inside a patient, the structure including at least one surface for coating, the method including the steps of:
cleaning the at least one surface to provide a cleaned surface;
functionalising the cleaned surface by subjecting the cleaned surface to acidification by citric acid to form a citric acid functionalised surface;
washing the citric acid functionalised surface to form a citric acid functionalised, washed surface, wherein the washing includes rinsing the citric acid functionalised surface in water until a thickness of a layer of the citric acid is reduced to a minimum thickness achievable by rinsing the at least one surface of the medical device in water and at the end of said rinsing the citric acid functionalised, washed surface exhibits a neutral pH;
drying the citric acid functionalised, washed surface to dry the layer of the citric acid, the layer of the citric acid having a thickness of up to 2.2 nanometers; and
applying a bioactive agent layer directly on so as to overlie the layer of the citric acid.

16. A method according to claim 15, wherein the cleaning the at least one surface includes contacting the at least one surface with a sodium hydroxide solution, wherein the washing the acid functionalised surface includes washing with water, and wherein the method also includes a step of rinsing the at least one surface after the contacting and before the functionalising.

17. A method according to claim 15, wherein the medical device comprises a stent providing the at least one surface or a balloon catheter having a balloon providing the at least one surface.

18. A method according to claim 17, wherein the bioactive agent layer includes paclitaxel.

19. A method according to claim 1, wherein the washing step is conducted sufficiently to provide a layer of the carboxylic acid that is one carboxylic acid molecule thick.

20. A method according to claim 15, wherein the layer of the citric acid is one citric acid molecule thick.

* * * * *